United States Patent [19]
Quallich

[11] Patent Number: 6,005,133
[45] Date of Patent: Dec. 21, 1999

[54] ENANTIOSELECTIVE OXAZABOROLIDINE CATALYSTS

[75] Inventor: George Joseph Quallich, North Stonington, Conn.

[73] Assignee: Pfizer Inc., New York, N.Y.

[21] Appl. No.: 08/530,363

[22] Filed: Oct. 10, 1995

Related U.S. Application Data

[63] Continuation of application No. 08/061,895, May 14, 1993, abandoned.
[51] Int. Cl.$^6$ .............................. C07F 5/04; C07C 27/04
[52] U.S. Cl. .......................... 558/289; 546/339; 549/401; 548/110; 564/10; 564/355; 568/1; 568/808; 568/814; 568/878
[58] Field of Search ........................ 558/289; 548/110; 568/808, 1, 814, 878; 546/339; 549/401; 564/355, 10

[56] References Cited

U.S. PATENT DOCUMENTS

| | | | |
|---|---|---|---|
| 3,137,723 | 6/1964 | Pribyl et al. | 260/55.1 |
| 4,749,809 | 6/1988 | Yoneyoshi | 558/384 |
| 4,923,999 | 5/1990 | Yoneyoshi | 548/268 |
| 4,943,635 | 7/1990 | Corey | 546/13 |

FOREIGN PATENT DOCUMENTS 171175  2/1986  European Pat. Off. .

OTHER PUBLICATIONS

Itsuno et al., Journal of the Chemical Society, Chemical Communications, 1983, 469–70.
Martens et al., Tetrahedron: Asymmmetry, 3, 347–50 (1992).
Matsunaga et al., Tetrahedron Letters, 32, 7715–18 (1991).
Tanaka et al., Journal of the Chemical Society, Chemical Communications, 1991, 1311–12.
Reetz et al., Angew. Chemie., Int. Ed. Eng. 26, 1141–3 (1987).
Didier et al., Tetrahedron, 47, 4941–58 (1991).
Brown et al., Tetrahedron: Asymmetry, 1, 869–72 (1990).
Brown et al., Tetrahedron: Asymmetry, 3 261–66 (1992).
Corey et al., Tetrahedron Letters, 30, 5547–50 (1989).
Corey et al., Tetrahedron Letters, 30, 6257–78 (1989).
Cho et al., Tetrahedron: Asymmetry, 3, 1539–42 (1992).
Brooks et al., Organic Mass Spectrometry, 2, 1023–32 (1969).
Brown et al., Accounts of Chemical Research, 25, 16–24 (1992).
Cho et al., Tetrahedron: Asymmetry, 3, 1583–90 (1992).
Brooks, et al., Chemical Abstracts, 72, 26317v (1970).
Mskinley et al., Chemical Abstracts, 80, 96307f (1980).
Berenguer et. al., Tetrahedron Asymmetr, vol. 4, No. 1, pp. 13–16, Jan. 1993.

*Primary Examiner*—Shailendra Kumar
*Attorney, Agent, or Firm*—Peter C. Richardson; Gregg C. Benson; Robert T. Ronau

[57] ABSTRACT

The enantioselective borane reduction of prochiral ketones to optically pure alcohols is effectively achieved by performing the reduction in the presence of catalytic amounts of the new and valuable oxazaborolidine compounds of formulae (I) and (II). The compounds of formulae (I) and (II) may be isolated and purified prior to use in the reduction reactions or the compounds of formulae (I) and (II) may be generated in situ.

4 Claims, No Drawings

ENANTIOSELECTIVE OXAZABOROLIDINE CATALYSTS

CROSS REFERENCE TO RELATED APPLICATIONS

This application is the national stage of International Application No. PCT/IB94/00066, having an international filing date of Apr. 12, 1994, which is a continuation of U.S. application Ser. No. 08/061,895, filed May 14, 1993, now abandoned.

BACKGROUND OF THE INVENTION

This invention relates to the enantioselective reduction of prochiral ketones using a borane reducing agent in the presence of a novel and valuable chiral oxazaborolidine catalyst and to certain of said chiral oxazaborolidine catalysts useful in said reduction.

The enantioselective reduction of prochiral ketones to yield substantially enantiomerically pure alcohols has long been a goal of synthetic organic chemists. A number of reagents have been reported which effect such a transformation. (See, for example, Corey, U.S. Pat. No. 4,943,635, the subject matter of which is incorporated herein by reference). However, these methods suffer from one or more of the following drawbacks: (a) unacceptable amounts of the undesired enantiomer present as an impurity with the product; (b) low yields of alcohol; (c) difficulty of carrying out the reaction; (d) expense of preparing the catalyst; (e) difficulty in preparing the catalyst; or (f) inapplicability to a wide range of substituted prochiral ketones.

In Corey, supra, and Merck, European Patent Application Nos. 0 453 288 A1 and 0 453 298 A2, enantioselectively effective oxazaborolidine catalysts are disubstituted at the $C_5$ carbon atom of formula (I) below. When said carbon atom is not disubstituted, the degree of enantioselection has been reported to be much lower (see Martens, et al., Tetrahedron:Asymmetry, 3, 347–50 (1992)).

In copending application PCT/US93/00687, it is disclosed that cis diphenyl substituted oxazaborolidines are useful catalysts for the enantioselective reduction of prochiral ketones to optically active alcohols. Disubstitution at the $C_5$ carbon atom was shown therein to be unnecessary. To obtain high enantiomeric excess in the reduction of prochiral ketones it is of primary importance that one face of the oxazaborolidine catalyst is completely blocked.

It is therefore an object of this invention to provide cis dialkyl, cis C-4 alkyl, C-5 phenyl and cis C-4 phenyl, C-5 alkyl substituted chiral oxazaborolidine compounds which are capable of directing the enantioselective reduction of prochiral ketones to generate substantially enantiomerically pure alcohols.

It is a further object of this invention to provide said chiral oxazaborolidine compounds which are easily prepared from relatively inexpensive starting materials or readily available starting materials.

It is a still further object of this invention to provide a method of using said chiral oxazaborolidine compounds as catalysts for the enantioselective reduction of prochiral ketones to afford substantially enantiomerically pure alcohols.

SUMMARY OF THE INVENTION

This invention provides a chiral oxazaborolidine compound of the formula

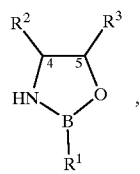

I wherein $R^1$ is hydrogen or heterocyclyl; $R^2$ and $R^3$ are syn; $R^2$ is $(C_1-C_8)$alkyl, benzyl, heterocyclyl or phenyl optionally substituted independently with up to three $(C_1-C_8)$alkyl, $(C_1-C_8)$alkoxy or halo groups; and $R^3$ is $(C_1-C_8)$alkyl, benzyl, heterocyclyl or phenyl optionally substituted independently with up to three $(C_1-C_8)$alkyl, $(C_1-C_8)$alkoxy or halo groups; provided that (a) $R^2$ and $R^3$ are not identical when one of $R^2$ or $R^3$ is phenyl optionally substituted independently with up to three $(C_1-C_8)$alkyl, $(C_1-C_8)$alkoxy or halo and that (b) when $R^2$ is $CH_3$ and $R^3$ is phenyl, $R^1$ is H.

Particularly preferred compounds of this invention are the compounds of formula (I) of this invention wherein $R^2$ is $(C_1-C_8)$alkyl and $R^3$ is benzyl, heterocyclyl or phenyl optionally substituted independently with up to three $(C_1-C_8)$alkyl, $(C_1-C_8)$alkoxy or halo groups. Still more particularly preferred are the compounds within this group wherein $R^2$ is methyl and $R^3$ is phenyl and especially (4R, 5S)-4-methyl-5-phenyl-1,3,2-oxazaborolidine and (4S, 5R)-4-methyl-5-phenyl-1,3,2-oxazaborolidine.

Also preferred are the compounds of formula (I) wherein $R^2$ is benzyl, heterocyclyl or phenyl optionally substituted independently with $(C_1-C_8)$alkyl, $(C_1-C_8)$alkoxy or halo groups.

This invention further provides a chiral oxazaborolidine of the formula

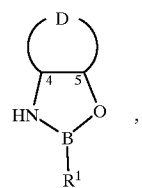

II wherein $R^1$ is hydrogen, $(C_1-C_8)$alkyl, benzyl, heterocyclyl or phenyl optionally substituted independently with up to three $(C_1-C_8)$alkyl, $(C_1-C_8)$alkoxy or halo groups; D is a cis-fused 4–6 membered carbomonocyclic ring optionally substituted independently with up to three $(C_1-C_8)$alkyl, heterocyclyl or phenyl optionally substituted independently with up to three $(C_1-C_8)$alkyl, $(C_1-C_8)$alkoxy or halo groups; a cis-fused 6–9 membered carbobicyclic system optionally substituted independently with up to three $(C_1-C_8)$alkyl, heterocyclyl or phenyl optionally substituted independently with up to three $(C_1-C_8)$alkyl, $(C_1-C_8)$alkoxy or halo groups; or a cis-fused system having the structure

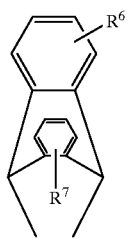

wherein $R^6$ and $R^7$ are each independently H, $(C_1-C_8)$alkyl, $(C_1-C_8)$alkoxy or halo.

Particularly preferred compounds within this invention are the compounds of formula (II) described in the preceding paragraph wherein D is a cis-fused 7 membered carbobicyclic system. Even more particularly preferred are the compounds within the preferred group wherein D is

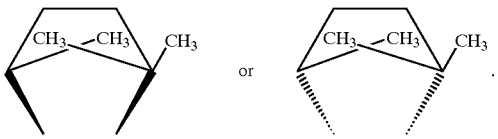

This invention still further provides the reactive intermediate borane compounds of the formula

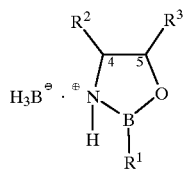

III wherein $R^1$ is hydrogen or heterocyclyl; $R^2$ and $R^3$ are syn; $R^2$ is $(C_1-C_8)$alkyl, benzyl, heterocyclyl or phenyl optionally substituted independently with up to three $(C_1-C_8)$alkyl, $(C_1-C_8)$alkoxy or halo groups; and $R^3$ is $(C_1-C_8)$alkyl, benzyl, heterocyclyl or phenyl optionally substituted independently with up to three $(C_1-C_8)$alkyl, $(C_1-C_8)$alkoxy or halo groups; provided that (a) $R^2$ and $R^3$ are not identical when one of $R^2$ or $R^3$ is phenyl optionally substituted independently with up to three $(C_1-C_8)$alkyl, $(C_1-C_8)$alkoxy or halo and that (b) when $R^2$ is $CH_3$ and $R^3$ is phenyl, $R^1$ is H.

This invention yet further provides the reactive intermediate borane compounds of the formula

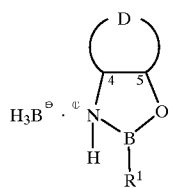

IV wherein $R^1$ is hydrogen, $(C_1-C_8)$alkyl, benzyl, heterocyclyl or phenyl optionally substituted independently with up to three $(C_1-C_8)$alkyl, $(C_1-C_8)$alkoxy or halo groups; D is a cis-fused 4–6 membered carbomonocyclic ring optionally substituted independently with up to three $(C_1-C_8)$alkyl, heterocyclyl or phenyl optionally substituted independently with up to three $(C_1-C_8)$alkyl, $(C_1-C_8)$alkoxy or halo groups; a cis-fused 6–9 membered carbobicyclic ring optionally substituted independently with up to three $(C_1-C_8)$alkyl, heterocyclyl or phenyl optionally substituted independently with up to three $(C_1-C_8)$alkyl, $(C_1-C_8)$alkoxy or halo groups; or a cis-fused system having the structure

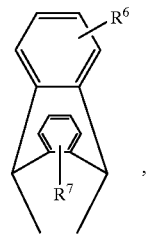

wherein $R^6$ and $R^7$ are each independently H, $(C_1-C_8)$alkyl, $(C_1-C_8)$alkoxy or halo.

The invention is also directed to a process for enantioselectively reducing a prochiral ketone comprising reacting said ketone with a borane reducing agent in the presence of a chiral oxazaborolidine catalyst of formula $(I_A)$,

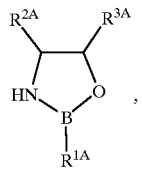

$(I_A)$ wherein $R^{1A}$ is hydrogen, $(C_1-C_8)$alkyl, benzyl, heterocyclyl or phenyl optionally substituted independently with up to three $(C_1-C_8)$alkyl, $(C_1-C_8)$alkoxy or halo groups; $R^{2A}$ and $R^{3A}$ are syn; $R^{2A}$ is $(C_1-C_8)$alkyl, benzyl, heterocyclyl or phenyl optionally substituted independently with up to three $(C_1-C_8)$alkyl, $(C_1-C_8)$alkoxy or halo groups; and $R^{3A}$ is $(C_1-C_8)$alkyl, benzyl, heterocyclyl or phenyl optionally substituted independently with up to three $(C_1-C_8)$alkyl, $(C_1-C_8)$alkoxy or halo groups; provided that (a) $R^{2A}$ and $R^{3A}$ are not identical when one of $R^{2A}$ or $R^{3A}$ is phenyl optionally substituted independently with up to three $(C_1-C_8)$alkyl, $(C_1-C_8)$alkoxy or halo and that (b) when $R^{2A}$ is $CH_3$ and $R^{3A}$ is phenyl, $R^{1A}$ is H, or formula (II) in a reaction inert solvent at a temperature of from about −20° C. to about 50° C. for about 5 minutes to about 24 hours.

A particularly preferred process within the scope of the above process is the process wherein the oxazaborolidine catalysts of formula (I) or formula (II) of the invention are generated in situ.

It will be recognized that the novel compounds of this invention of formula (I) are within the scope of the oxazaborolidine compounds of formula $(I_A)$ of this invention all of which are useful as enantioselective catalysts in borane reductions of prochiral ketones.

DETAILED DESCRIPTION OF THE INVENTION

The compounds of formulas (I), $(I_A)$ and (II) of this invention are readily prepared. Thus a single enantiomer of a 1,2-substituted-2-aminoethanol is suspended in a reaction inert solvent such as tetrahydrofuran, xylene, toluene, benzene, chlorobenzene or the like and is heated to a temperature of from about 60° C. to about boiling, preferably at about 60° C. The reaction mixture is stirred for from about 5 minutes to about 15 minutes at this temperature; preferred is the amount of time necessary to obtain complete dissolution of the disubstituted aminoethanol derivative. The reaction mixture is then treated with borane, a trialkyl boroxine, an alkyl boronic acid or an aryl boronic acid and is cooled to room temperature. Suitable boroxines for this reaction include boroxines of the formula

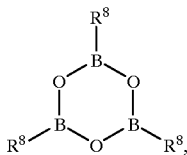

V wherein $R^8$ is $(C_1-C_8)$alkyl, benzyl, heterocyclyl or phenyl substituted with up to three $(C_1-C_8)$alkyl, $(C_1-C_8)$alkoxy or halo groups. The reaction mixture is stirred for about one hour to about 24 hours, preferably for about 18 hours at room temperature. The oxazaborolidine compound of formula (I), formula ($I_A$) or formula (II) is then isolated by the removal of water and excess boroxine or evolution of hydrogen when borane is employed and utilizing the standard techniques well known to one of ordinary skill in the art of synthetic organic chemistry.

The optically pure 1,2-disubstituted erythro α-amino alcohols are commercially available or, in the alternative, can be readily prepared. Thus, to prepare the compounds of formula (I) or ($I_A$), the optically pure 1,2-disubstituted erythro α-amino alcohol can be prepared by the method disclosed in Reetz et al., Angew. Chemie. Int. Ed. Eng., 26, 1141–43 (1987). To prepare the compounds of formula (II), the requisite optically pure cyclic or bicyclic α-amino alcohol can be prepared by the method disclosed in Matsunaga et al., Tetrahedron Letters, 32, 7715–18 (1991).

The boroxine derivatives used herein are also readily prepared when not readily available. Reaction of a trialkyl- or triarylborane with boron oxide under reflux for about 24 hours to about 48 hours in an inert atmosphere conveniently prepares the trialkyl or triarylboroxine derivatives. Alternatively, reaction of borane, a trialkyl borate or a triarylborate with a suitable Grignard reagent of the formula $R^8$-Mg-X wherein $R^8$ is $(C_1-C_8)$alkyl, benzyl, or phenyl optionally substituted with up to three $(C_1-C_8)$alkyl, $(C_1-C_8)$alkoxy or halo groups such as chloro or fluoro in a suitable reaction inert solvent such as tetrahydrofuran or diethyl ether at about –20° C. to about 50° C. affords the $R^8$-substituted boronic acid upon workup. Continued reflux utilizing a Dean-Stark trap to remove water generates the $R^8$-substituted boroxine derivative.

The boronic acids which are used herein are well known in the art. Therefore the boronic acids can be prepared by the method recited by Corey, supra or according to the well known methods cited in references therein.

The process of the present invention is carried out by reacting a prochiral ketone of the formula $R^4R^5CO$, wherein $R^4$ and $R^5$ are defined hereinbelow with a borane reducing agent in the presence of a chiral oxazaborolidine catalyst according to formula (I), formula ($I_A$) or formula (II). Said process results in the enantioselective reduction of said prochiral ketone, such that only one of two possible alcohol enantiomers is formed in preference to the corresponding enantiomer. The degree of enantio-selectivity which is obtained will vary depending upon the size of the $R^4$ and $R^5$ groups attached to the carbonyl group forming the prochiral ketone. When the $R^4$ and $R^5$ groups are similar in size, the degree of enantioselection will be lower. As the $R^4$ and $R^5$ groups become increasingly disparate in size, the degree of enantio-selection will be greater. However, it should be understood that the size of the $R^4$ and $R^5$ groups is not the sole determining factor affecting the degree of enantioselectivity achieved. Ordinarily, with prochiral ketones wherein $R^4$ and $R^5$ are at least moderately different in size, at least 90% of the desired enantiomer will be obtained. However, typically greater than 90% of the desired enantiomer is obtained The prochiral ketone is dissolved in a suitable reaction inert solvent such as toluene, diethyl ether, dioxane, tetrahydrofuran or the like. Preferred is tetrahydrofuran. A catalytically effective amount of a chiral oxazaborolidine compound of formula (I), formula ($I_A$) or formula (II) is added to the reaction mixture at from about –78° C. to about room temperature, preferably at room temperature; however, the preferred temperature will vary depending upon the particular borane reducing agent being used. The preferred amount of said catalyst is about 5–10 mole % with respect to said ketone. The reaction mixture is then treated slowly with about 2.1 hydride equivalents of a borane reducing agent such as borane dimethylsulfide complex, borane tetrahydrofuran complex, catecholborane or the like. When the prochiral ketone contains an $R^4$ or $R^5$ group which bears a borane-coordinating functionality, additional hydride equivalents of reducing agent are necessary. Generally preferred for its ease of use is borane dimethylsulfide complex. Generally the reducing agent is added at a rate which modulates the rate of the catalytic reduction. The reaction is sometimes complete as soon as all of the reducing agent has been added, as can be determined by monitoring the course of the reaction via thin layer chromatography according to the standard practice of organic chemistry. However, occasionally it will be desirable to allow the reaction mixture to stir for longer periods of time such as overnight, or to heat the reaction mixture to temperatures of up to 40° C. to 65° C. in order to ensure completion of the reaction. Additionally, with some substrates and reducing agents, it may be necessary to stir the reaction mixture at –78° C. for a lengthy period of time such as 16 hours. Ordinarily the reaction mixture is stirred at about room temperature for about fifteen minutes. The temperature of reaction mixture is then adjusted to 0° C. and quenched with a proton source. Said proton source, usually a lower alkanol such as methanol, is added slowly to control the exothermic reaction. The product is isolated by removing the solvent in vacuo followed by partitioning between an organic solvent and an aqueous acid followed by separation of layers and purification according to the standard techniques of organic chemistry.

The particularly preferred process of the invention is carried out by reacting a prochiral ketone of the formula $R^4R^5CO$, wherein $R^4$ and $R^5$ are defined hereinbelow, with a borane reducing agent in the presence of a chiral oxazaborolidine catalyst according to formula (I), formula ($I_A$) or formula (II), generated in situ from an aminoalcohol derivative. Thus an aminoalcohol derivative of the formula $H_2NCHR^2CHR^3OH$, wherein $R^2$ and $R^3$ are defined hereinabove, is dissolved under an inert atmosphere at room temperature in a suitable reaction inert solvent such as diethyl ether, toluene, dioxane, tetrahydrofuran or the like. Preferred are toluene and tetrahydrofuran. The reaction mixture is then treated with a borane reducing agent such as borane methyl sulfide complex or borane tetrahydrofuran complex. Preferred is borane methylsulfide complex. The reaction mixture is stirred for 6–24 hours and a prochiral ketone of the formula $R^4R^5CO$ is added slowly, over a period of 30 minutes to about 2 hours, depending upon the amount of the prochiral ketone being added. The reaction mixture is stirred for an additional 5–30 minutes and is then cooled to 0° C. and quenched with a proton source. Ordinarily, a lower alkanol such as methanol is advantageously employed as the proton source. The product is isolated by following standard procedures known to one of ordinary skill in the art.

The prochiral ketone may be any compound of the formula $R^4R^5CO$ wherein $R^4$ and $R^5$ are different and wherein $R^4$ and $R^5$ are inert to reduction by borane. Additionally, if enough reducing agent is utilized to account for the presence of borane coordinating substituents on $R^4$ or $R^5$, then $R^4$ or $R^5$ may be thus substituted. Thus, $R^4$ and $R^5$ may independently be any organic radicals, e.g. alkyl, aryl, alkenyl and may be taken together to form a ring system so that $R^4R^5CO$ is cyclic, e.g. tetralone. Additionally, $R^4$ and $R^5$ may be independently substituted with any substituents such as alkyl, alkenyl, aryl, alkoxy, halo, etc. It will be understood by one of ordinary skill in the art that when $R^4$ or $R^5$ contains an alkenyl substituent it will be necessary to choose a borane reducing agent which is not capable of hydroborating the olefin. Further, said $R^4$ and $R^5$ groups may be substituted with boron-coordinating substituents provided that enough reducing agent is utilized to account for such substitution. Examples of borane-coordinating substituents which may be present are amino and certain heteroaryl groups such as thiazolyl, oxazolyl, pyridyl and the like. One of ordinary skill in the art would recognize that additional equivalents of borane reducing agent will be necessary when borane-coordinating substituents are present on said $R^4$ or $R^5$ groups.

The compounds of formula (III) and formula (IV) of the present invention are reaction intermediates which exist during the course of the reaction. A compound of either formula (III) or (IV) is formed upon the addition of the borane reducing agent to the reaction mixture containing the oxazaborolidine catalyst and the substrate and is a result of the reaction of said catalyst with said borane reducing agent.

Thus, the oxazaborolidine compounds are useful as enantioselective catalysts for the reduction of prochiral ketones to afford substantially enantiomerically pure alcohols. The process of preparing said alcohols has great utility since the optically pure form of a compound often has far different reactivity or usefulness in biological systems. The optically pure alcohols thus prepared may find utility as intermediates in the synthesis of a pharmaceutical, agricultural or other useful product. The optically pure alcohols thus prepared may themselves be useful as pharmaceuticals, agricultural products or the like.

The following terms and phrases, when used herein and in the appendant claims, are defined as follows:

1. "Alkyl" means a branched or unbranched saturated hydrocarbon group containing the specified number of carbon atoms, e.g., $C_1$–$C_8$. Examples include, but are not limited to methyl, ethyl, isopropyl, n-butyl, t-butyl and the like.

2. "Alkenyl" means a branched or unbranched unsaturated hydrocarbon group containing one or more double bonds and the specified number of carbon atoms, e.g., $C_2$–$C_4$. Examples include, but are not limited to vinyl, ethylidene, allyl and the like.

3. "Alkoxy" means a branched or unbranched saturated hydrocarbon containing the specific number of carbon atoms and a single oxygen atom by which said hydrocarbon is attached to a central backbone. Examples include, but are not limited to methoxy, ethoxy and the like.

4. "Heterocyclyl" means a 5- or 6-membered aromatic group containing up to three heteroatoms, each of said heteroatoms selected from N, O and S and which may be optionally benzo-fused, said heterocyclyl group being optionally substituted independently with up to three $(C_1$–$C_8)$alkyl, $(C_1$–$C_8)$alkoxy or halo groups.

5. A "prochiral ketone", denoted by $R^4R^5CO$, is a ketone in which $R^4$ and $R^5$ are non-identical, so that the secondary alcohol reduction product $R^4R^5CHOH$ has a chiral center at the alcohol carbon. For cyclic prochiral ketones, it is understood that $R^4$ and $R^5$ are taken together, forming a ring including the ketone, and that the ring so formed has no plane of symmetry across a plane drawn perpendicular to the plane containing the carbonyl group and the two carbon atoms attached directly thereto, said plane containing both the carbon and oxygen atoms of the carbonyl group as points therein.

6. Reaction inert solvent means a solvent which does not interact with the reactants, intermediates or products in such a way that adversely affects the yield of the desired products.

7. "Syn" means that the substituents substituted on adjacent ring carbon atoms are located on the same side of a plane which encompasses the bond between said carbon atoms and the bonds by which each of said carbon atoms are attached to the ring.

8. "Enantiomeric excess", or e.e., is the excess of one of two enantiomers over the other, usually expressed as a percentage, i.e., a 90% e.e. reflects the presence of 95% of one enantiomer and 5% of the other in the material in question.

9. A "borane-coordinating substituent" is a functional group which has the ability to donate an electron pair to boron forming a coordinate bond with said boron. Typical examples include, but are not limited to, amines and various nitrogen-containing heterocycles.

10. "Hydride equivalents" means the number of hydride, or $H^\ominus$, ions which are generated from one mole of a given reagent, e.g., one mole of borane-tetrahydrofuran complex generates three moles of hydride ion and is thus considered to contain three hydride equivalents.

11. "Catalytically effective" means that substoichiometric amount of a material which is sufficient to facilitate the conversion of a reactant to the desired product (s).

12. "Ambient temperature" means the temperature of the immediate external environment surrounding the reaction flask. This temperature is usually room temperature (20°–25° C.).

13. In situ is the reaction condition wherein the chiral oxazaborolidines of formula (I) or formula (II) of the invention are formed from the precursor aminoalcohol and borane. The prochiral ketone is added after the oxazaborolidine is generated. The chiral oxazaborolidines of the invention are not isolated under these conditions.

14. "Carbomonocyclic" means a monocyclic ring containing the number of indicated carbon atoms.

15. "Carbobicyclic" means any bicyclic system containing the indicated number of carbon atoms.

The present invention is illustrated by the following examples. However, it should be understood that the invention is not limited to the specific details of these examples. All reactions are conducted under an inert atmosphere, such as nitrogen or argon, unless otherwise specified. All solvents are anhydrous, i.e., contain such a small amount of water that said water does not interact with the reagents, intermediates or products in such a way that adversely affects the yield of the desired products. Where used herein, "THF" means tetrahydrofuran.

EXAMPLE 1

The (4R, 5S) Compound of Formula (I) wherein $R^1$ is H, $R^2$ is $CH_3$ and $R^3$ is phenyl To a solution of commercially available (1S, 2R)-(+)-norephedrine (14.67 g, 97 mmol) in THF (16 mL) at 0° C. was added borane methylsulfide complex (2M in THF, 48.5 mL, 97 mmol) over 1 hr. The reaction was stirred 16 hrs, heated to 120° C. to distill off the THF and dimethylsulfide, and cooled to afford the title product as a white solid. $^1$H NMR ($C_6D_6$)δ; 7.18–6.97(m, 5H), 5.46(d, J=8 Hz, 1H), 4.10(dq, J=8 Hz, J=6 Hz, 1H), 0.92(d, J=6 Hz, 3H). $^{13}$C NMR ($CDCl_3$)δ 139.4, 128.0, 127.4, 126.1, 84.4, 53.9, 19.6.

EXAMPLE 2

In situ Preparation of the Title Compound of Example 1 and Reduction of α-tetralone Borane methylsulfide complex (neat, ~10M, 1.4 mL, 14 mmol) was added to a solution of (1S, 2R)-(+)-norephedrine (151 mg, 1 mmol) in THF (70 mL) at ambient temperature and stirred for 16 hrs. α-Tetralone (2.92 g, 19.7 mmol) as a solution in THF (10 mL) was added to the preceding solution over 1 hr, stirred for 15 min after addition was completed, was cooled to 0° C., and quenched with methanol (27 mL). After stirring the quenched reaction for 18 hrs, the solvents were removed under vacuum, the residual oil was dissolved in methylene chloride (50 mL), washed with pH 4 phosphate buffer (50 mL), water (50 mL), treated with magnesium sulfate, and the solvent was removed under vacuum to give 2.88 g (95% yield) of (S) tetralol. 82% ee (91:9 ratio of enantiomers).

EXAMPLE 3

Preparation of the Compound of Formula ($I_A$) wherein $R^1$ is Me, $R^2$ is $CH_3$ and $R^3$ is phenyl (1S, 2R)-(+)-Norephedrine (7.78 g, 51 mmol), toluene (150 mL), and trimethylboroxine (4.8 mL) were combined at ambient temperature and stirred for 5 days. Water, toluene and excess boroxine were distilled off until about 70 mL volume remained. The reaction was chased with toluene (3×90 mL), and the remainder of toluene removed under vacuum to afford the oxazaborolidine as a pale yellow oil (8.71 g, 98%). $^1$H NMR ($C_6 D_6$)δ; 7.36–6.98 (m, 5H), 5.33(d, J=8 Hz, 1H), 3.43 (dq, J=8 Hz, J=6 Hz 1H), 2.72 (bs, 1H), 0.37 (s, 3H), 0.36(d, J=6 Hz, 3H). To a solution of α-tetralone (2.92 g, 19.7 mmol), THF (80 mL), and the oxazaborolidine derived from norephedrine (218 mg, 1.2 mmol) under a nitrogen atmosphere was added borane methylsulfide complex (2M in THF, 7.0 mL, 14 mmol) over 75 min. After the addition was complete, the contents stirred for an additional 15 min, cooled to 0° C., and quenched with methanol (27 mL). After stirring the quenched reaction for 18 hrs the solvents were removed under vacuum, the residual oil was dissolved in methylene chloride (50 mL), washed with pH 4 phosphate buffer (50 mL), water (50 mL), treated with magnesium sulfate, and the solvent was removed under vacuum to give 3.16 g (80% ee) of the (S) tetralol as a colorless oil.

EXAMPLE 4

In situ Preparation of the Compound of Formula (II) wherein $R^1$ is

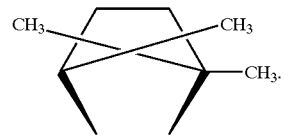

Borane methylsulfide complex (neat, ~10M, 1.4 mL, 14 mmol) was added to a solution of cis, exo-3-amino-2-hydroxybornane [J. Chem. Soc. (C) 49 1970] (169 mg, 1 mmol) in THF (70 mL) at ambient temperature and stirred for 16 hrs. α-Tetralone (2.92 g, 19.7 mmol) as a solution in THF (10 mL) was added to the preceding solution over 1 hr, stirred for 15 min after addition was completed, cooled to 0° C., and quenched with methanol (27 mL). After stirring the quenched reaction for 18 hrs, the solvents were removed under vacuum, the residual oil was dissolved in methylene chloride (60 mL), and washed with pH 4 phosphate buffer (50 mL), water (50 mL), treated with magnesium sulfate, and the solvent was removed under vacuum to give the (R) tetralol 2.89 g (97% yield) 84% ee.

EXAMPLE 5

In situ Preparation of the Compound of Formula (II) wherein $R^1$ is

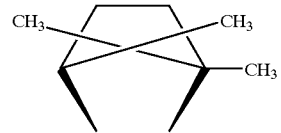

Borane methylsulfide complex (neat, ~10M, 1.4 mL, 14 mmol) was added to a solution of cis, exo-3-amino-2-hydroxybornane [J. Chem. Soc. 49, 1970] (169 mg, 1 mmol) in THF (70 mL) at ambient temperature and was stirred for 16 hours. Acetophenone (2.36 g, 24.6 mmol) as a solution in THF (10 mL) was added to the preceding solution over one hour, stirred for fifteen minutes after addition was completed, cooled to 0° C., and quenched with methanol (27 mL). After stirring the quenched reaction for 18 hours, the solvents were removed under vacuum, the residual oil was dissolved in methylene chloride (50 mL), washed with pH 4 phosphate buffer (50 mL), water (50 mL), treated with magnesium sulfate, and the solvent was removed under vacuum to give the (R) phenethyl alcohol. 2.17 g (92% yield) 88% ee.

EXAMPLE 6

Preparation of the Compound of Formula (II) wherein $R^1$ is $CH_3$

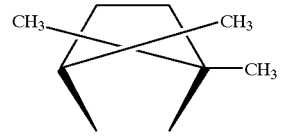

Cis, exo-3-amino-2-hydroxybornane (1.0 g, 5.9 mmol), toluene (18 mL), and trimethylboroxine (0.56 mL) were combined at ambient temperature and stirred for 16 hr. Water, toluene and excess boroxine were distilled off until about 8 mL volume remained. The reaction was chased with toluene (3×11 mL), and the remainder of toluene removed under vacuum to afford the oxazaborolidine as a pale yellow oil (1.10 g, 98%). To a solution of α-tetralone (2.92 g, 19.7 mmol), THF (80 mL), and the oxazaborolidine derived from cis, exo-3-amino-2-hydroxybornane (228 mg, 1.2 mmol) under a nitrogen atmosphere was added borane methylsulfide complex (2M in THF, 7.0 mL, 14 mmol) over 75 min. After the addition was complete, the contents stirred for an additional 15 min, cooled to 0° C., and quenched with methanol (27 mL). After stirring the quenched reaction for 18 hrs the solvents were removed under vacuum, the residual oil was dissolved in methylene chloride (50 mL), washed with pH 4 phosphate buffer (50 mL), water (50 mL), treated with magnesium sulfate, and the solvent was removed under vacuum to give the (R) tetralol as a colorless oil 3.16 g (90% ee).

EXAMPLE 7

In situ Preparation of the (4S, 5R) Compound of Formula (I) wherein $R^1$ is H, $R^2$ is t-butyl and $R^3$ is phenyl and Reduction of α-tetralone Borane methylsulfide complex (neat, ~10M, 0.44 mL, 4.4 mmol) was added to a solution of (1R, 2S)-2-tert-butyl-2-aminophenylethanol [Angew. Chem. Int. Ed. Engl. 26 1141 (1987)] (120 mg, 0.62 mmol) in THF (22 mL) at ambient temperature and stirred for 16 hrs; α-Tetralone (906 mg, 6.2 mmol) as a solution in THF (3 mL) was added to the preceding solution over a 1 hr, stirred for 15 min after addition was completed, cooled to 0° C., and quenched with methanol (20 mL). After stirring the quenched reaction for 18 hrs, the solvents were removed under vacuum, the residual oil was dissolved in methylene chloride (30 mL), washed with pH 4 phosphate buffer (30 mL), water (30 mL), treated with magnesium sulfate, and the solvent was removed under vacuum to give the (R) tetralol 841 mg (91% yield) 82% ee.

EXAMPLE 8

Preparation of the (4S, 5R) Compound of Formula ($I_A$) wherein $R^1$ is $CH_3$, $R^2$ is t-butyl and $R^3$ is phenyl and Reduction of α-tetralone (1R, 2S)-2-tert-butyl-2-aminophenylethanol (1.0 g, 5.2 mmol), toluene (16 mL), and trimethylboroxine (0.50 mL) were combined at ambient temperature and stirred for 16 hr. Water, toluene and excess boroxine were distilled off until about 8 mL volume remained. The reaction was chased with toluene (3×10 mL), and the remainder of toluene removed under vacuum to afford to oxazaborolidine as a pale yellow oil (1.10 g, 98%). To a solution of α-tetralone (2.92 g, 19.7 mmol), THF (80 mL), and the oxazaborolidine derived from (1R, 2S)-2-tert-butyl-2-aminophenylethanol (228 mg, 1.2 mmol) under a nitrogen atmosphere was added borane methylsulfide complex (2M in THF, 7.0 mL, 14 mmol) over 75 min. After the addition was complete, the contents were stirred for an additional 15 min, cooled to 0° C., and quenched with methanol (27 mL). After stirring the quenched reaction for 18 hrs the solvents were removed under vacuum, the residual oil was dissolved in methylene chloride (50 mL), washed with pH 4 phosphate buffer (50 mL), water (50 mL), treated with magnesium sulfate, and the solvent was removed under vacuum to give the (R) tetralol as a colorless oil 3.1 g (90% ee).

EXAMPLES 9–18

Using substantially the same procedure as recited in Example 2, but substituting the indicated prochiral ketone for α-tetralone, the alcohols of the following ketones were prepared.

| | STARTING KETONE | EE | ABSOLUTE STEREO-CHEMISTRY OF ALCOHOL |
|---|---|---|---|
| 9. | α-tetralone | 82 | (S) |
| 10. | acetophenone | 84 | (S) |
| 11. | propiophenone (Et) | 78 | (S) |
| 12. | α-chloroacetophenone (Cl) | 88 | (R) |
| 13. | pivalophenone (t-Bu) | 80 | (R) |
| 14. | 3-acetylpyridine | 90 | (S) |
| 15. | chroman-4-one | 90 | (S) |
| 16. | pinacolone | 78 | (S) |
| 17. | 2-hexanone | 68 | (S) |

| STARTING KETONE | EE | ABSOLUTE STEREO-CHEMISTRY OF ALCOHOL |
|---|---|---|
| 18. 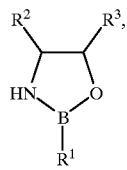 | 88 | (S) |

I claim:
1. A chiral oxazaborolidine of the formula

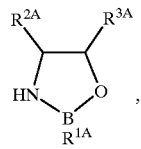

(I)

wherein:
R$^1$ is hydrogen or heterocyclyl;
R$^2$ and R$^3$ are syn;
R$^2$ is benzyl, heterocyclyl or phenyl optionally substituted independently with up to three (C$_1$–C$_8$)alkyl, (C$_1$–C$_8$)alkoxy or halo groups; and
R$^3$ is benzyl, heterocyclyl or phenyl optionally substituted independently with up to three (C$_1$–C$_8$)alkyl, (C$_1$–C$_8$)alkoxy or halo groups; provided that R$^2$ and R$^3$ are not identical when one of R$^2$ or R$^3$ is phenyl optionally substituted independently with up to three (C$_1$–C$_8$)alkyl, (C$_1$–C$_8$)alkoxy or halo groups.

2. A compound according to claim 1 wherein R$^2$ is benzyl, heterocyclyl or phenyl optionally substituted independently with up to three (C$_1$–C$_8$)alkyl, (C$_1$–C$_8$)alkoxy or halo groups.

3. A method for stereoselectively reducing a prochiral ketone to a substantially enantiomerically pure alcohol comprising reacting said prochiral ketone with a borane reducing agent in the presence of a chiral oxazaborolidine according to the formula (I$_A$), (IA)

wherein R$^{1A}$ is hydrogen, (C$_1$–C$_8$)alkyl, benzyl, heterocyclyl or phenyl optionally substituted independently with up to three (C$_1$–C$_8$)alkyl, (C$_1$–C$_8$)alkoxy or halo groups; R$^{2A}$ and R$^{3A}$ are syn; R$^{2A}$ is benzyl, heterocyclyl or phenyl optionally substituted independently with up to three (C$_1$–C$_8$)alkyl, (C$_1$–C$_8$)alkoxy or halo groups; R$^{3A}$ is benzyl, heterocyclyl or phenyl optionally substituted independently with up to three (C$_1$–C$_8$)alkyl, (C$_1$–C$_8$)alkoxy or halo groups; provided that R$^{2A}$ and R$^{3A}$ are not identical when one of R$^{2A}$ or R$^{3A}$ is phenyl optionally substituted with up to three (C$_1$–C$_8$)alkyl, (C$_1$–C$_8$)alkoxy or halo groups.

4. The method according to claim 3 wherein the chiral oxazaborolidine is generated in situ.

* * * * *